United States Patent
Liu et al.

(10) Patent No.: US 10,823,653 B2
(45) Date of Patent: Nov. 3, 2020

(54) ROCK DAMAGE MECHANICS TEST SYSTEM FOR HIGH TEMPERATURE AND HIGH PRESSURE DEEP EARTH ENVIRONMENT

(71) Applicant: Sichuan University, Chengdu (CN)

(72) Inventors: Jianfeng Liu, Chengdu (CN); Heping Xie, Chengdu (CN); Jianliang Pei, Chengdu (CN); Wenxi Fu, Chengdu (CN); Jianhui Deng, Chengdu (CN); Zhide Wu, Chengdu (CN); Huining Xu, Chengdu (CN); Lu Wang, Chengdu (CN); Fei Wu, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 15 days.

(21) Appl. No.: 16/396,772

(22) Filed: Apr. 29, 2019

(65) Prior Publication Data
US 2019/0331569 A1    Oct. 31, 2019

(30) Foreign Application Priority Data

Apr. 28, 2018  (CN) .......................... 2018 1 0404424

(51) Int. Cl.
*G01N 3/18* (2006.01)
*G01N 33/24* (2006.01)
*G01N 3/06* (2006.01)

(52) U.S. Cl.
CPC ............... *G01N 3/062* (2013.01); *G01N 3/18* (2013.01); *G01N 33/24* (2013.01); *G01N 2203/0256* (2013.01); *G01N 2203/0605* (2013.01)

(58) Field of Classification Search
CPC .. G01N 3/02; G01N 3/12; G01N 3/10; G01N 2203/069; G01N 2203/0256; G01N 2203/0226; G01N 33/24; G01N 2203/0232
See application file for complete search history.

(56) References Cited

U.S. PATENT DOCUMENTS

| | | | |
|---|---|---|---|
| 7,143,653 B2* | 12/2006 | Abdel-Hadi | G01N 3/10 73/819 |
| 2005/0150273 A1* | 7/2005 | Potter | G01N 3/10 73/38 |
| 2018/0335494 A1* | 11/2018 | Hakimuddin | G01R 33/46 |

* cited by examiner

*Primary Examiner* — Brandi N Hopkins
(74) *Attorney, Agent, or Firm* — Bayramoglu Law Offices LLC

(57) ABSTRACT

A rock damage mechanics test system for high temperature and high pressure deep earth environment includes an MTS triaxial test machine and a control system connected therewith. The MTS triaxial test machine is composed of a rigid frame, a high temperature and high pressure triaxial chamber, and a triaxial chamber base. The control system includes a workstation for data processing and a manual controller for controlling the workstation and a master controller. The system improves mounting and dismounting efficiency of an MTS triaxial force sensor, enhances reliability of lifting and solves the problem of aligning holes during the force sensor mounting process, thus improving the mounting efficiency.

8 Claims, 6 Drawing Sheets

ROCK DAMAGE MECHANICS TEST SYSTEM FOR HIGH TEMPERATURE AND HIGH PRESSURE DEEP EARTH ENVIRONMENT

CROSS REFERENCE TO RELATED APPLICATIONS

This application is based upon and claims priority to Chinese Patent Application No. 201810404424.2, filed on Apr. 28, 2018 the entire contents of which are incorporated herein by reference.

TECHNICAL FIELD

The invention belongs to the field of rock mechanics test of engineering rock masses, in particular to a rock damage mechanics test system for high temperature and high pressure deep earth environment.

BACKGROUND

Triaxial tests and other laboratory rock mechanics tests are necessary basic tests for all kinds of rock engineering. Rock mechanics triaxial tests at high temperature and high pressure are also extremely important for all kinds of rock engineering in depth earth. Therefore, the reliable rock damage mechanics tests at simulated high temperature and high pressure in deep earth are of great significance for the rock engineering in depth earth. As the core load sensor for rock damage mechanics tests at simulated high temperature and high pressure in deep earth, the accurate measurement of the high temperature and high pressure load sensor is of crucial importance. Considering the high temperature and high pressure and other special and complex test conditions, the high temperature and high pressure load sensors are more likely to have breakdown in practical use. Therefore, the load sensors are required to be checked, maintained and replaced at a relatively short interval. The MTS rock mechanics test system is one of the world's most advanced and widely used rock mechanics equipment. However, the system has complex and special structure that its triaxial chamber is hollow and narrow in space, and a solid rigid column and a high temperature and high pressure load sensor are arranged from top to bottom, in sequence. An upper end of the solid rigid column and the solid steel load frame are connected by means of high-strength bolts. The high temperature and high pressure load sensor and a lower end of the solid rigid column are connected by means of a bolt and limited by means of a stop pin. Precise row lines (e.g. high temperature, high pressure and seepage) are densely arranged on the base of the triaxial chamber. Therefore, it is difficult and risky to dismount and mount the high temperature and high pressure load sensor in the triaxial chamber. The difficulties are as follows: firstly, the high temperature and high pressure load sensor is heavy and hard to be manually lifted for a long time in a stable manner; secondly, it is difficult for simultaneous alignment of a bolt hole and a stop pin hole of the high temperature and high pressure load sensor in the triaxial chamber due to the limited operation space; and thirdly, with the presence of unstable suction force between the high temperature and high pressure load sensor and the rigid column, the high temperature and high pressure load sensor is difficult to be dismounted and has a high risk of abrupt falling. The risk is that the sophisticated and expensive high temperature and high pressure load sensor is easy to be dropped and damaged due to instability of manual lifting, and drop of the sensor caused by sudden loss of unstable suction force and unstable lifting may lead to damages to the precise row lines of the triaxial chamber base as well as personal and mechanical injuries to operators. Obviously, the manual lifting of prior art for dismounting, alignment and mounting is risky and difficult in operation.

SUMMARY

The technical problem to be solved by the invention is to provide a rock damage mechanics test system for high temperature and high pressure deep earth environment, so as to improve mounting and dismounting efficiency of an MTS triaxial force sensor, enhance reliability of lifting and solve the problem of aligning holes during the force sensor mounting process to improve the mounting efficiency.

The technical solution of the invention is a rock damage mechanics test system for high temperature and high pressure deep earth environment, comprising an MTS triaxial test machine and a control system connected therewith. The MTS triaxial test machine is composed of a rigid frame, a high temperature and high pressure triaxial chamber and a triaxial chamber base; the control system comprises a workstation, a master controller and a manual controller; the master controller is connected with the workstation and the manual controller; and the master controller is configured to control a confining pressure control system, a temperature control system, a seepage control system and a loading control system. The rock damage mechanics test system for high temperature and high pressure deep earth environment is characterized in that the MTS triaxial test machine comprises an accurate triaxial force sensor limiting hole alignment device 2 and an MTS triaxial force sensor dismounting and mounting supporting device 1; and the accurate triaxial force sensor limiting hole alignment device 2 is arranged above the MTS triaxial force sensor dismounting and mounting supporting device 1.

The MTS triaxial force sensor dismounting and mounting supporting device comprises a force sensor lifting seat and a jack propped upon an MTS hydraulic servo table and configured to jack up the force sensor lifting seat.

The force sensor lifting seat comprises a connecting disk connected with the jack, a support disk configured to support an MTS triaxial force sensor and an operation channel for dismounting and mounting an MTS triaxial force sensor; a groove dented downwards is arranged above the connecting disk, the support disk is disposed in the groove and freely propped upon the connecting disk, and the support disk is radially limited by side walls of the groove; both the connecting disk and the support disk are in an annular shape with a through hole arranged at the middle, and the through holes of the connecting disk and the support disk form a control operation channel; and a limiting device is arranged to prevent the MTS triaxial force sensor from disengaging from the support disk.

The accurate triaxial force sensor limiting hole alignment device comprises a master rod for aligning with a central threaded hole and a secondary rod for aligning with a limiting hole; the master rod and the secondary rod are kept in a horizontal level, with a center-to-center distance therebetween equal to a center-to-center distance between a central threaded hole and a peripheral limiting hole; a stop sleeve is sleeved on the master rod to keep the master rod and the secondary rod in a horizontal level and the center-to-center distance between the master rod and the secondary rod equal to the center-to-center distance between the central threaded hole and the peripheral limiting hole; the stop sleeve is cylindrical; two corbel structures are arranged on the stop sleeve, i.e., an upper corbel and a lower corbel; an end round hole axis of the upper corbel coincides with an end round hole axis of the lower corbel; the end round hole axis of the upper corbel and the end round hole axis of the lower corbel are parallel to the axis of the master rod; a circular magnetic block is fixed on a secondary rod body, the circular magnetic block is configured to adsorb a hole alignment sleeve sleeved on the secondary rod body; an inner diameter of the hole alignment sleeve equals an inner diameter of a steel pin in an limiting hole arranged on the sensor; the hole alignment sleeve are marked with a first scale line and a second scale line; the first scale line corresponds to a relaxed or an aligned state, and the second scale line corresponds to a contracted or an aligning state; and the secondary rod comprises a secondary rod head body and the secondary rod body, and the secondary rod head body is connected with the secondary rod body by means of a spring.

Further, a flange protruding upward is arranged at the middle of the groove in an axial direction thereof, and the flange, an inner wall of the groove and a bottom of the groove are enclosed to form an circular slideway; the flange is peripherally sleeved with a round rod slidable in the slideway; and the support disk is freely propped upon the round rod.

Further, the limiting device is a stop collar, and the stop collar is arranged above the connecting disk and detachably connected with the connecting disk; an inner wall of the stop collar and an upper surface of the support disk are enclosed to form an accommodating cavity fitting with the MTS triaxial force sensor; and a locking member is arranged on the stop collar to lock a relative position of the force sensor.

Further, the inner wall of the stop collar extends inwards in the radial direction thereof and protrudes into the groove of the connecting disk; and the support disk is vertically limited by a bottom surface of the protrusion of the stop collar extending inwards.

Further, the locking member is a stop screw radially arranged along the stop collar and running through the stop collar, and the stop screw and the stop collar are in threaded connection.

Further, the jack comprises a bottom pedestal, a top support table and a jacking mechanism arranged therebetween and driving the support table to move up and down; the jacking mechanism comprises four transmission rods, and every two of the four transmission rods form an elbowed transmission member, each of the elbowed transmission members is provided with a connecting lug; two transmission rods of each of the elbowed transmission members are hinged with the connecting lug; the two elbowed transmission members are oppositely arranged to form a parallelogram structure with equal side length, one end of the parallelogram structure is hinged with a bottom lug arranged on the pedestal, and the other end thereof is hinged with a top lug arranged on the support table; a connecting lug is provided for every two of the transmission rods; and a first threaded rod is arranged diagonally to the parallelogram structure, and the first threaded rod and the connecting lug are in threaded connection to drive the elbowed transmission members to stretch and draw back.

Further, the connecting lug is a grooved member with a groove structure for accommodating the corresponding transmission rod; the bottom lug is a grooved member with a groove structure for accommodating the corresponding transmission rod; and the top lug is also a grooved member with a groove structure for accommodating the corresponding transmission rod.

Further, the support table is connected with the connecting disk by means of a group of support rods; and the support rods are threaded, nuts fitting with the threads are fixedly attached to an upper surface and a lower surface of the support table, and the support rods run through the support table and are in threaded connection with the nuts on the upper and lower surfaces of the support table.

Further, a plane mirror is arranged on the upper surface of the support table, and the operation channel and an orthographic projection of the plane mirror on the upper surface of the support table are matched; and the plane mirror is hinged to the support table by means of a spherical hinge.

Further, a locating hole fitting with a central alignment pin of the MTS hydraulic servo table is arranged on the pedestal.

Further, the secondary rod body and the upper corbel are fixed by means of a horizontal cylindrical pin.

Further, the master rod is composed of a second threaded rod, a smooth cylinder and a smooth cylinder with a horizontal hole; and the second threaded rod can rotate into a threaded hole at a lower end of a solid rigid column of the MTS triaxial chamber, the smooth cylinder is arranged in the middle of the master rod, and the stop sleeve is sleeved on the smooth cylinder.

Further, a horizontal cylindrical short rod is arranged on the master rod by running through a round hole configured on the smooth cylinder with the horizontal hole of the master rod; and after insertion of the horizontal cylindrical short rod into the round hole configured on the smooth cylinder with the horizontal hole, the master rod can be rotated to allow the second threaded rod rotate into the threaded hole at the lower end of the solid rigid column of the MTS triaxial chamber.

Further, the secondary rod body of the secondary rod is a cylindrical rod; a rolling steel ball is arranged in the secondary rod head body at an upper part of the secondary rod; and an outer diameter of the secondary rod head body is smaller than an inner diameter of the peripheral limiting hole.

Further, the spring is a cylindrical compression spring.

The beneficial effects of the invention are as follows: The invention replaces the method for dismounting and mounting the load sensor with the manual lifting, economizes on manpower, improves the efficiency of dismounting and mounting and provides stable and powerful support for the load sensor to effectively prevent accidental falling damages of the load sensor and other secondary damages. The groove dented downwards is arranged above the connecting disk, the support disk is disposed in the groove and freely propped upon the connecting disk, and the support disk is radially limited by side walls of the groove, thus the support disk can only rotate around the axis thereof. As a result, the bolt hole of the load sensor can be aligned with a mounting hole on the solid steel column by rotating the support disk for convenient and accurate bolting. An observation system with controllable direction and adjustable tilt angle is arranged to realize the visualized dismounting and mounting states of sensors in the triaxial chamber. The holes of the load sensor and the solid rigid column are aligned in a simple and reliable manner. After the hole on the secondary rod is aligned, the hole alignment sleeve is lowered down to insert the lower section of the master rod into the center hole of the load sensor, and then the load sensor is rotated to sleeve the stop pin of the load sensor with the hole alignment sleeve, thus the center hole of the load sensor is aligned with the limiting hole of the solid rigid column.

Marks in the figures: force sensor lifting seat 1A, jack 2A, connecting disk 11A, groove 111A, flange 112A, slideway 113A, support disk 12A, round rod 121A, operation channel 13A, stop collar 14A, accommodating cavity 15A, stop screw 141A, pedestal 21A, locating hole 211A, support table 22A, transmission rod 23A, connecting lug 24A, bottom lug 25A, top lug 26A, first threaded rod 27A, support rod 3A, nut 31A, plane mirror 4A, MTS hydraulic servo table 5A, horizontal cylindrical short rod 1B, master rod 2B, stop sleeve 3B, secondary rod body 4B, hole alignment sleeve 5B, circular magnetic block 6B, horizontal cylindrical pin 7B, spring 8B, secondary rod head body 9B, rolling steel ball 10B, upper scale line 11B, lower scale line 12B, solid rigid column 13B, secondary rod 14B, upper corbel 15B, lower corbel 16B, second threaded rod 17B, smooth cylinder 18B, smooth cylinder 19B with a horizontal hole, secondary rod body 20B, accurate triaxial force sensor limiting hole alignment device 2, and MTS triaxial force sensor dismounting and mounting supporting device 1.

DETAILED DESCRIPTION OF THE EMBODIMENTS

Figure 1:
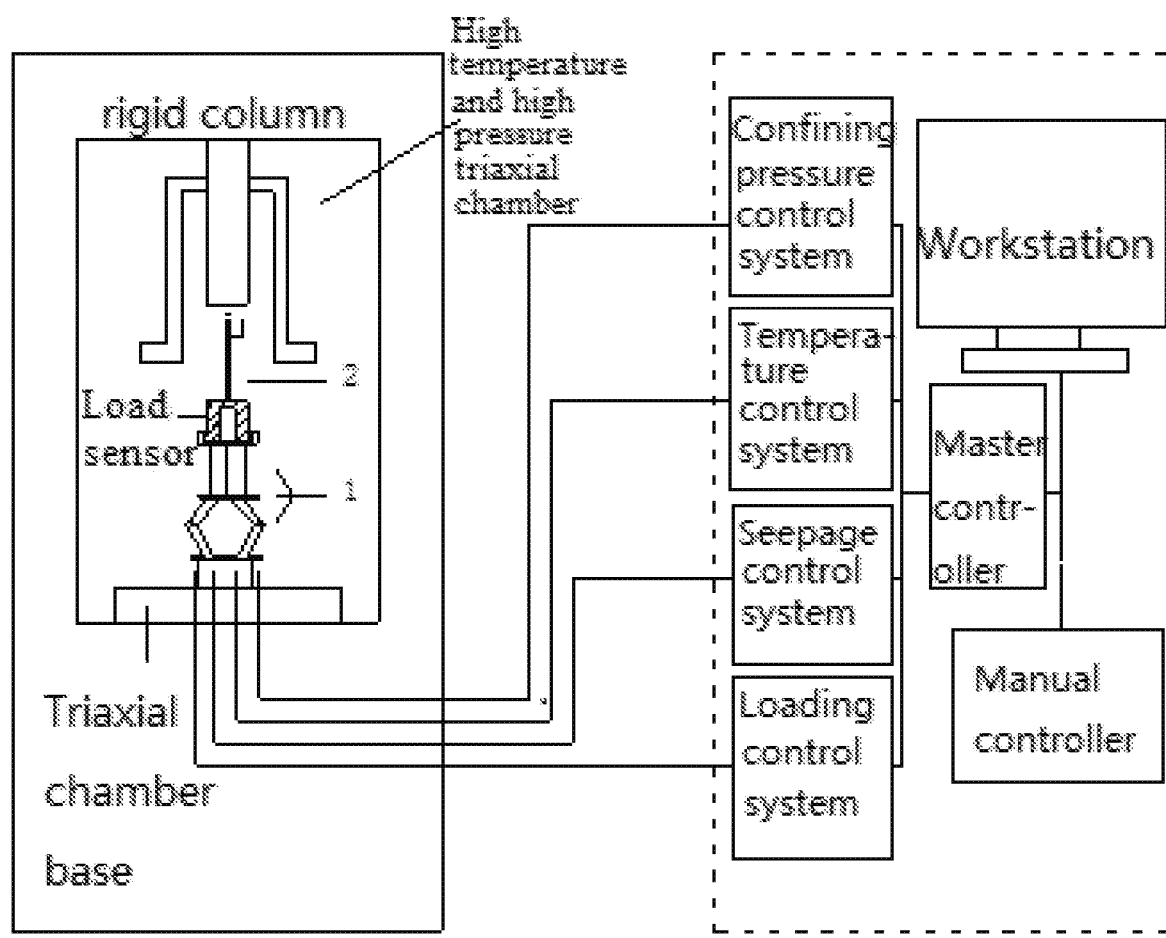
FIG. 1 is a schematic diagram of the rock damage mechanics test system for high temperature and high pressure deep earth environment

The invention will be further described in combination with drawings and embodiments:

As shown in FIG. 1:

A rock damage mechanics test system for high temperature and high pressure deep earth environment, comprising an MTS triaxial test machine and a control system connected therewith.

The MTS triaxial test machine is composed of a rigid frame, a high temperature and high pressure triaxial chamber and a triaxial chamber base. The high temperature and high pressure triaxial chamber and the triaxial chamber base are arranged on the rigid frame. The high temperature and high pressure triaxial chamber is vertically opposite to the triaxial chamber base, with a central axis of the high temperature and high pressure triaxial chamber coincides with a central axis of the triaxial chamber base.

The control system comprises a workstation for data processing, a manual controller for controlling the workstation and a master controller; the workstation and the manual controller are synchronously connected with the master controller; and the master controller is configured to control a confining pressure control system, a temperature control system, a seepage control system and a loading control system.

The MTS triaxial test machine further comprises an accurate triaxial force sensor limiting hole alignment device 2 and a MTS triaxial force sensor dismounting and mounting supporting device 1; and the accurate triaxial force sensor limiting hole alignment device 2 is arranged above the MTS triaxial force sensor dismounting and mounting supporting device 1.

Figure 2:
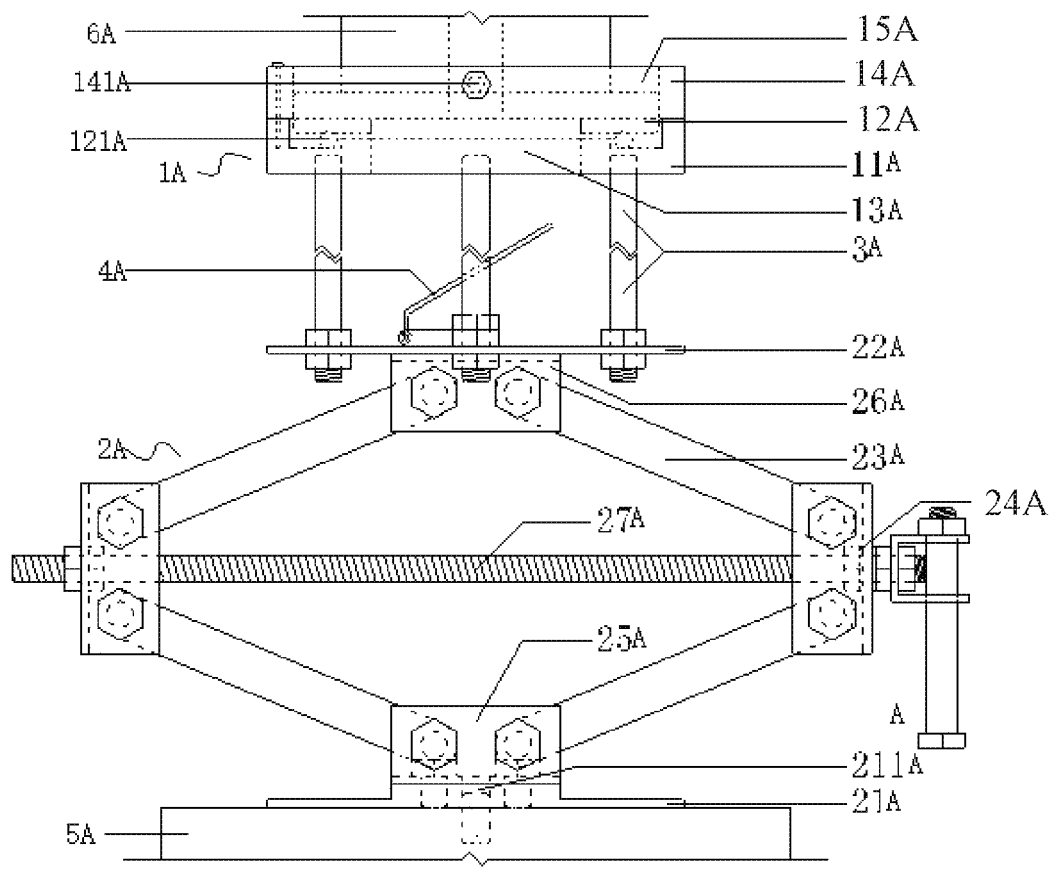
FIG. 2 is a structural diagram of the MTS triaxial force sensor dismounting and mounting supporting device.
Figure 3:
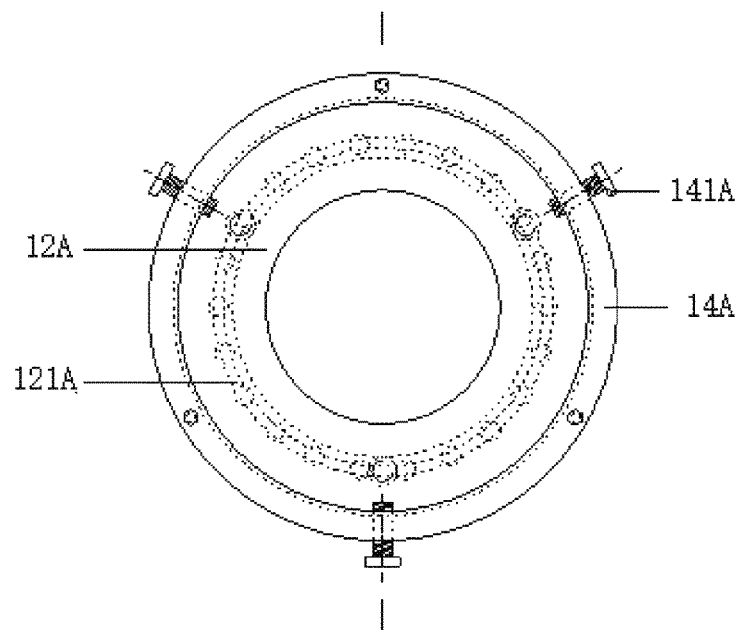
FIG. 3 is a structural diagram of the force sensor lifting seat.
Figure 4:
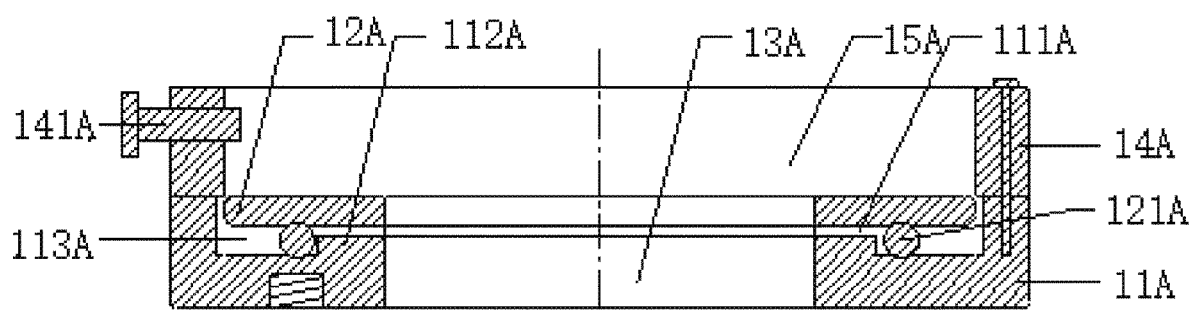
FIG. 4 is an A-A sectional view of FIG. 1.

As shown in FIGS. 2 to 4, a platform for rock mechanics test in high temperature and high pressure deep earth environment, comprising a force sensor lifting seat 1A and a jack 2A propped upon an MTS hydraulic servo table 5A and configured to jack up the force sensor lifting seat 1A.

The force sensor lifting seat 1A comprises a connecting disk 11A connected with the jack 2A, a support disk 12A configured to support an MTS triaxial force sensor and an operation channel 13A for dismounting and mounting the MTS triaxial force sensor; a groove 111A dented downwards is arranged above the connecting disk 11A, the support disk 12A is disposed in the groove 111A and freely propped upon the connecting disk 11A, and the support disk 12A is radially limited by side walls of the groove 111A; both the connecting disk 11A and the support disk 12A are in an annular shape with a through hole arranged at the middle, and the through holes of the connecting disk 11A and the support disk 12A form a control operation channel 13A; and a limiting device is arranged to prevent the MTS triaxial force sensor from disengaging from the support disk 12A.

According to the invention, the force sensor lifting seat 1A is configured to jack up the force sensor and propped upon the jack 2A, and the force sensor is lifted to the mounting position by jacking up the force sensor lifting seat 1A by means of the jack 2A, or withdrawn from a rigid column of a triaxial chamber by jacking down the force sensor lifting seat 1A by means of the jack 2A.

The connecting disk 11A of the lifting seat 1A is connected with the jack 2A, and the support disk 12A is configured to support the MTS triaxial force sensor. The support disk 12A is freely propped upon the connecting disk 11A, that is, the support disk 12A is limited by the underneath connecting disk 11A to prevent the support disk 12A from falling vertically. However, there is no connector or the like arranged between the support disk 12A and the connecting disk 11A, so they can move relatively in the radial direction or rotate in the axial direction. As the support disk 12A and the connecting disk 11A can move relatively, the support disk 12A arranged in a groove 111A of the connecting disk 11A can be radially limited by side walls of the groove 111A, so as to prevent the support disk 12A from disengaging from the connecting disk 11A when the support disk 12A moves in relative to the connecting disk 11A in the radial direction, thus the radial movement of the support disk 12A and the connecting disk 11A is limited, and the support disk 12A can only rotate around the axis thereof. As a result, a bolt hole of the force sensor can be aligned with a mounting hole on a solid steel column by rotating the support disk 12A for convenient and accurate bolting. The control operation channel 13A is formed by through holes of the connecting disk 11A and the support disk 12A. An operator can mount and remove screws through the operation channel 13A to expand operation space for mounting and dismounting, and avoid interference of related members in the force sensor lifting seat 1A that exists in the perpendicular mounting process, and eliminate deviations from the mounting position due to contact with the force sensor lifting seat 1A by the operator. Further, the dismounting and mounting of the force sensor with supporting device rather than manual support save both time and labor; and the force sensor is supported in a more stable and powerful manner, a certain pulling force can be applied to the force sensor after the force sensor and the support disk 12A are limited to effectively solve the problem that the force sensor is difficult to be dismounted in the presence of oil suction force, and to prevent the force sensor from accidental drop or damage.

As shown in FIGS. 2 to 4, to reduce frictional resistance between the connecting disk 11A and the support disk 12A, a flange 112A protruding upward is preferably arranged at the middle of the groove 111A in the axial direction, and the flange 112A, an inner wall of the groove 111A and a bottom of the groove 111A are enclosed to form an circular slideway 113A; the flange 112A is peripherally sleeved with a round rod 121A slidable in the slideway 113A; and the support disk 12A is freely propped upon the round rod 121A.

The round rod 121A is arranged between the connecting disk 11A and the support disk 12A to reduce friction surface and decrease the friction resistance. The round rod 121A is radially limited by the flange 112A, so that the round rod 121A can rotate in the axial direction around the flange 112A, and the support disk 12A is freely propped upon the round rod 121A to facilitate rotation movement of the support disk 12A.

The limiting device for preventing the MTS triaxial force sensor from disengaging from the support disk 12A can be a hoop encircling the force sensor and connected with the connecting disk 11A. However, the hoop encircling the force sensor can be mounted on or dismounted from the force sensor in the same procedure. As the hoop and the force sensor have large contact area, the probability of damaging the force sensor rises with the increased collision probability when they are mounted and dismounted.

As a preferred embodiment, as shown in FIGS. 2 and 4, the limiting device is a stop collar 14A, and the stop collar 14A is arranged above the connecting disk 11A and detachably connected with the connecting disk 11A; an inner wall of the stop collar 14A and an upper surface of the support disk 12A are enclosed to form an accommodating cavity 15A fitting with the MTSA triaxial force sensor; and a locking member is arranged on the stop collar 14A to lock a relative position of the force sensor.

To avoid uneven pressure on the support disk 12A by the force sensor, which leads to an upturned end of the support disk 12A and deviation of the force sensor axis from the mounting position, the inner wall of the stop collar 14A preferably extends inwards in the radial direction and protrudes into the groove 111A of the connecting disk 11A; and the support disk 12A is vertically limited by the bottom surface of the protrusion extending inwards of the stop collar 14A.

The locking member can be a sucker or the like, but sucking stability of the sucker depends on flatness of the force sensor surface and other factors. Preferably, the locking member is a stop screw 141A radially arranged along the stop collar 14A and running through the stop collar 14A, and the stop screw 141A and the stop collar 14A are in threaded connection. The stop screw 141A has characteristics of low cost, easy operation and strong adaptability.

As shown in FIG. 2, the jack 2A preferably comprises a bottom pedestal 21A, a top support table 22A and a jacking mechanism arranged therebetween and driving the support table 22A to move up and down; the jacking mechanism comprises four transmission rods 23A, and every two of the four transmission rods 23A form an elbowed transmission member; each of the elbowed transmission members is provided with a connecting lug 24A; two transmission rods 23A of each of the elbowed transmission members are hinged with the connecting lug 24A; the two elbowed transmission members are oppositely arranged to form a parallelogram structure with equal side length, one end of the parallelogram structure is hinged with a bottom lug 25A arranged on the pedestal 21A, and the other end thereof is hinged with a top lug 26A arranged on the support table 22A; a connecting lug 24A is provided for every two of the transmission rods 23A; and a first threaded rod 27A is arranged diagonally for the parallelogram structure, and the first threaded rod 27A and the connecting lug 24A are in threaded connection to drive the elbowed transmission members to stretch and draw back.

The force sensor lifting seat 1A is lifted up and down by rotating the first threaded rod 27A. The operation is simple and easy to be controlled, so the force sensor rises and falls conveniently and efficiently. The first threaded rod 27A can be manually driven or electrically driven.

Preferably, the connecting lug 24A is a grooved member with a groove structure for accommodating the corresponding transmission rod 23A; the bottom lug 25A is a grooved member with a groove structure for accommodating the corresponding transmission rod 23A; and the top lug 26A is also a grooved member with a groove structure for accommodating the corresponding transmission rod 23A. The connecting lug 24A, the bottom lug 25A and the top lug 26A can be members in various shapes, but grooved member provides greater strength.

The support table 22A is able to be directly connected with the connecting disk 11A, providing that a specified lifting range is achieved and the specification of the jack meets requirements. Preferably, the support table 22A is connected with the connecting disk 11A by means of a group of support rods 3A; the support rods 3A are threaded, nuts 31A fitting with the threads are fixedly attached to an upper surface and a lower surface of the support table 22A, and the support rods 3A run through the support table 22A and are in threaded connection with the nuts 31.

The support table 22A and the connecting disk 11A are connected by means of the support rod 3A and the nuts 31A, so that another lifting structure is formed between the support table 22A and the connecting disk 11A. Therefore, the requirements for specification of the jack 2A can be lowered. Once the support disk 12A deviates from the horizontal position, it can be centered by slightly adjusting the support rod 3A and the nuts 31A.

To conveniently observe positions of a limiting hole and a center hole on the bottom of the force sensor in the triaxial chamber, centering adjustment is directed to simplify the dismounting and mounting of the force sensor. As shown in FIG. 2, a plane mirror 4A is preferably arranged on the upper surface of the support table 22A, and the operation channel 13A and an orthographic projection of the plane mirror 4A on the upper surface of the support table 22A are matched; and the plane mirror 4A is hinged to the support table 22A by means of a spherical hinge. The plane mirror 4A is hinged to the support table 22A by means of the spherical hinge, so that the plane mirror 4A can pitch and rotate as required.

To mount the device by using the structure of the MTS test system, as shown in FIG. 2, a locating hole 211A fitting with a central alignment pin of an MTS hydraulic servo table 5A is preferably arranged on the pedestal 21A. When the device aligns with the MTS hydraulic servo table 5A and is fixed by bolts, on the one hand, the force sensor can be lifted up and down by lifting the device up and down, and on the other hand, the device and the force sensor can be lifted up and down together by a built-in loading system of the MTS if lifting motion of the device is limited.

Figure 5:
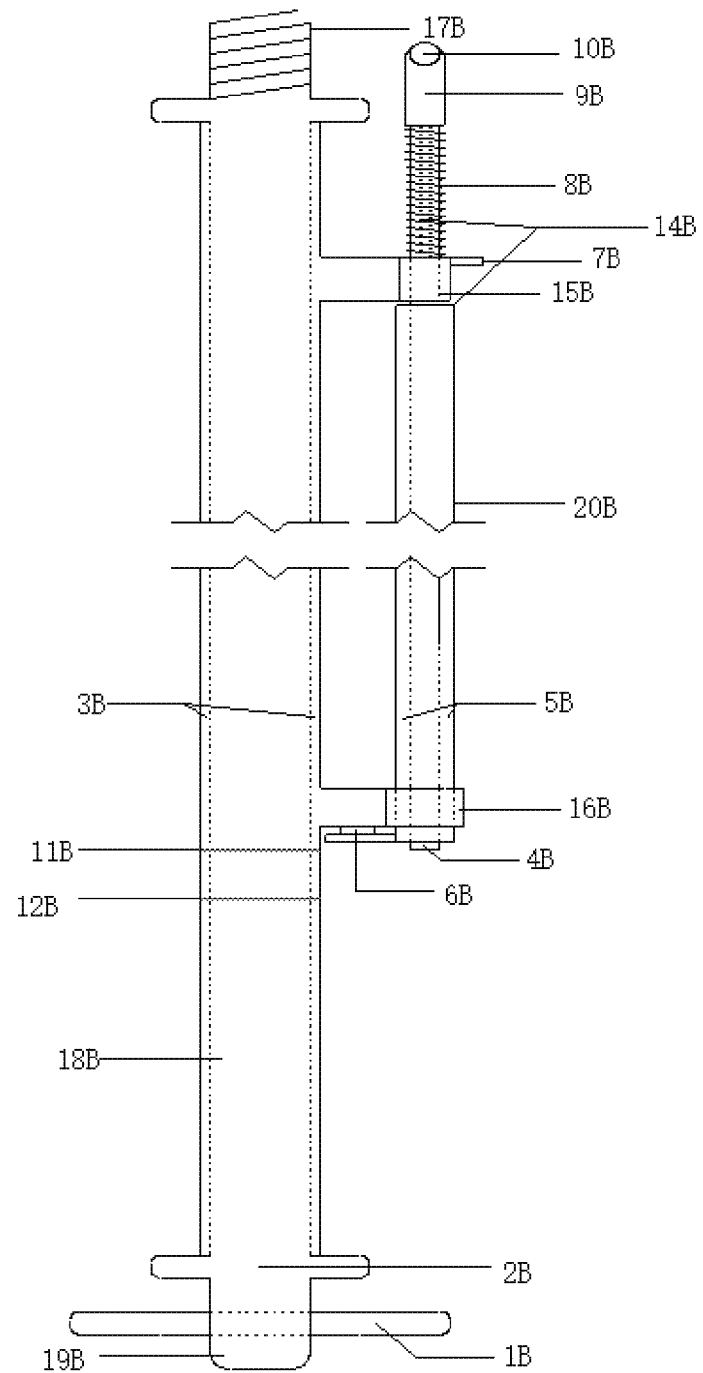
FIG. 5 is a structural diagram of an MTS triaxial high temperature and high pressure force sensor mounting device.

As shown in FIG. 5, the MTS triaxial sensor aligning and mounting device comprises a master rod 2B, a secondary rod 14B, a stop sleeve 3B, a hole alignment sleeve 5B and related accessory members; the master rod 2B is configured to align to a central threaded hole, and the secondary rod 14B is configured to align to a limiting hole. The cylindrical stop sleeve 3B is sleeved on the master rod 2B to keep the master rod 2B and the secondary rod 14B in a horizontal level and the center-to-center distance between the master rod 2B and the secondary rod 14B equals the center-to-center distance between the central threaded hole and the peripheral limiting hole. The rigid connection between the master rod 2B and the secondary rod 14B ensures that the master rod 2B and the secondary rod 14B are kept in a horizontal level and the center-to-center distance therebetween equals a center-to-center distance between the central threaded hole and the peripheral limiting hole. Both the central threaded hole and the peripheral limiting hole are arranged on the MTS test system, two corbel structures are arranged on the stop sleeve 3B, i.e., an upper corbel 15B and a lower corbel 16B; an end round hole axis of the upper corbel 15B coincides with an end round hole axis of the lower corbel 16B; the end round hole axis of the upper corbel 15B and the end round hole axis of the lower corbel 16B are parallel to the axis of the master rod 2B; a circular magnetic block 6B is fixed on the secondary rod 14B, the circular magnetic block 6B is configured to adsorb a hole alignment sleeve 5B sleeved on the secondary rod 14B; an inner diameter of the hole alignment sleeve 5B equals an inner diameter of a steel pin in an limiting hole arranged on the sensor; the hole alignment sleeve 5B are marked with a first scale line and a second scale line; the first scale line corresponds to a relaxed or an aligned state, and the second scale line corresponds to a contracted or an aligning state; and the master rod 2B is composed of a threaded rod 17B, a smooth cylinder 18B and a smooth cylinder 19B with a horizontal hole, the threaded rod 17B can rotate into a threaded hole at a lower end of a solid rigid column 13B of the MTS triaxial chamber, the smooth cylinder is arranged in the middle of the master rod 2B, and the stop sleeve 3B is sleeved on the smooth cylinder 18B.

A horizontal cylindrical short rod 1B is arranged on the master rod 2B by running through a round hole configured on the smooth cylinder 19B with the horizontal hole of the master rod 2B; and after insertion of the horizontal cylindrical short rod 1B into the round hole configured on the smooth cylinder 19B with the horizontal hole, the master rod 2B can be rotated to allow the threaded rod 17B rotate into the threaded hole at the lower end of the solid rigid column 13B of the MTS triaxial chamber.

The secondary rod 14B is composed of a secondary rod head body 9B and a secondary rod body 20B; the secondary rod body 20B is a cylindrical rod; the secondary rod head body 9B is connected with the secondary rod body 20B by means of a spring 8B; the secondary rod head body 9B arranged at an upper part of the secondary rod 14B is provided with a rolling steel ball 10B; an outer diameter of the secondary rod head body 9B is lower than the inner diameter of the peripheral limiting hole; the secondary rod head body 9B is capable of inserting into the limiting hole; the secondary rod body 20B is fixed on the upper corbel 15B by means of a horizontal cylindrical pin 7B; the body of the secondary rod 14B is cylindrical; the secondary rod head body 9B arranged at the upper part of the secondary rod 14B is provided with a rolling steel ball 10B; an outer diameter of the secondary rod head body 9B is lower than the inner diameter of the peripheral limiting hole; and the secondary rod head body 9B is capable of inserting into the limiting hole. The horizontal cylindrical short rod 1B is further arranged on the master rod 2B by running through a round hole configured on the smooth cylinder 19B with the horizontal hole of the master rod 2B; and after insertion of the horizontal cylindrical short rod 1B into the round hole configured on the smooth cylinder 19B with the horizontal hole, the master rod 2B can be rotated to allow the threaded rod 17B rotate into the threaded hole at the lower end of the solid rigid column 13B of the MTS triaxial chamber, and the horizontal cylindrical short rod 1B provides a point of external force application when the threaded rod 17B of the master rod 2B is rotated into the threaded hole.

The stop sleeve 3B is cylindrical and has two corbel structures, i.e., an upper corbel 15B and a lower corbel 16B; an end round hole axis of the upper corbel 15B coincides with an end round hole axis of the lower corbel 16B; and the end round axes of the upper corbel 15B and the lower corbel 16B are parallel to the axis of the master rod 2B.

The master rod 2B and the secondary rod 14B are kept in a horizontal level, with the center-to-center distance therebetween equal to the center-to-center distance between the central threaded hole and the peripheral limiting hole; the end round hole axis of the upper corbel 15B coincides with the end round hole axis of the lower corbel 16B; and the end round axes of the upper corbel 15B and the lower corbel 16B are parallel to the axis of the master rod 2B.

The secondary rod 14B is composed of a secondary rod head body 9B and a secondary rod body 20B; the secondary rod head body 9B is provided with a rolling steel ball 10B; an outer diameter of the secondary rod head body 9B is lower than an inner diameter of the peripheral limiting hole; and a horizontal cylindrical pin 7B is arranged on the secondary rod body 20B.

Preferably, the spring 8B can have spring bar and other contractile structures.

Figure 6:
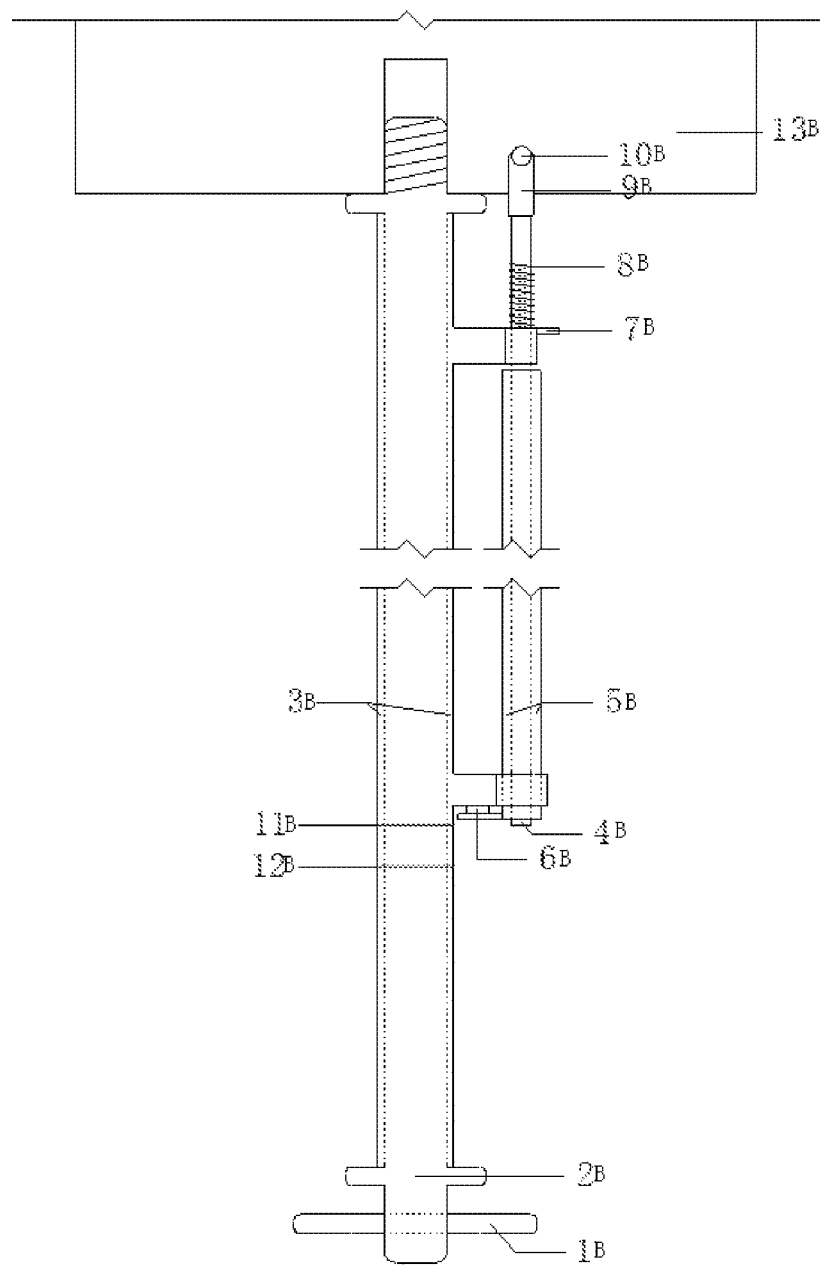
FIG. 6 shows a relaxed or aligned state of the accurate limiting hole alignment device.

FIG. 6 shows the relaxed or the aligned state of the accurate limiting hole alignment device. The lower end of the secondary rod body 4B is pointed at the upper scale line 11B, wherein the term "relaxed" means that the secondary rod 14B is retractable freely and the term "aligned" means that the secondary rod body 9B is inserted into the limiting hole at a lower end of the solid rigid column 13B. At the relaxed state, the spring 8B is free and the length thereof is equal to original length thereof; and at the aligned state, the spring 8B is subject to deformation but is not locked in position, thus the length thereof is smaller than the original length thereof.

Figure 7:
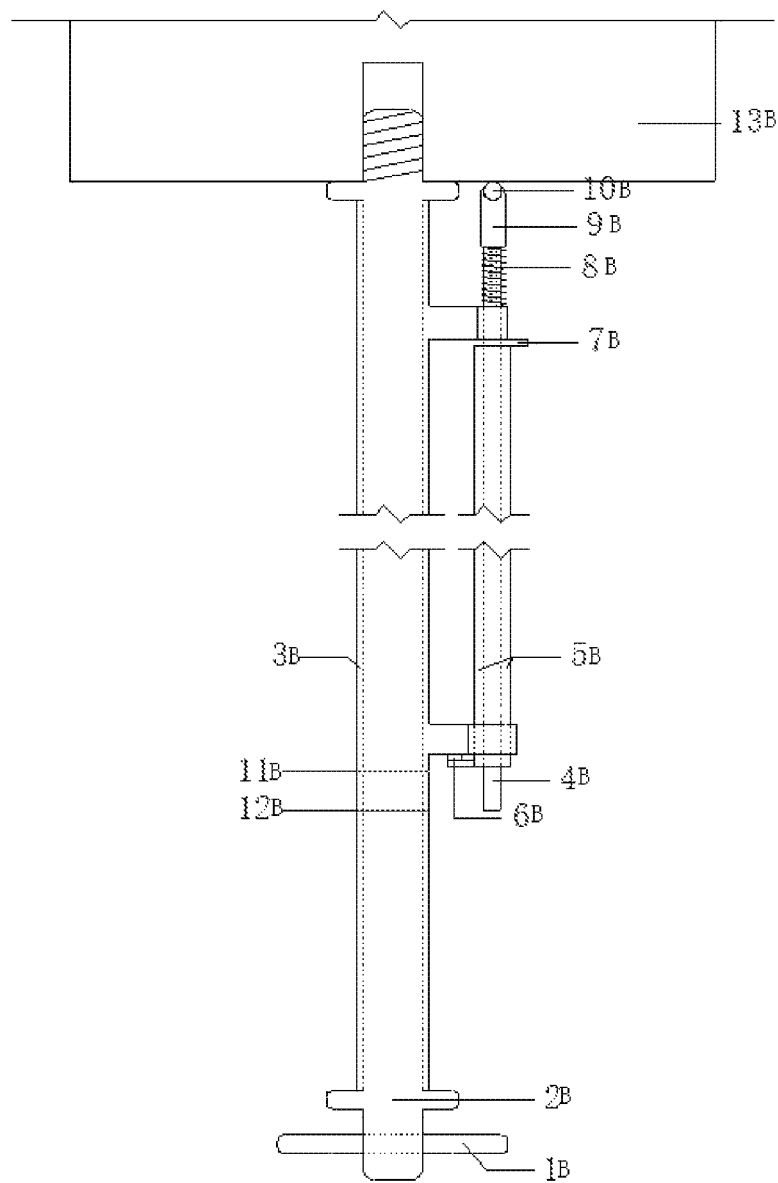
FIG. 7 shows a contracted or aligning state of the accurate limiting hole alignment device.

FIG. 7 shows the contracted or the aligning state of the accurate limiting hole alignment device. The secondary rod body 4B is pointed at the lower scale line 12B, wherein the term "contracted" means that the secondary rod is retracted to return the rod head from the limiting hole at a lower end of the solid rigid column 13B after alignment; and the term "aligning" means that the secondary rod aligns to the limiting hole during the rotation of the sleeve after the threaded section of the master rod is inserted into the central threaded hole at the lower end of the solid rigid column 13B. At the contracted state, the spring 8B is subject to elastic deformation that shortens the length thereof, thus the length of the spring 8B is smaller than the original length thereof at this time, and the spring is capable of being pushed out of the limiting hole; at the aligning state, the spring 8B is locked in position and is subject to the maximum elastic deformation, thus the length of the spring 8B is smaller than the original length thereof; and the maximum deformation maintained in the aligning process of the spring 8B is conductive to reducing torsional deformation of the spring 8B, decreasing displacement of the secondary rod head body 9B in the aligning process and improving aligning accuracy.

What is claimed is:

1. A rock damage mechanics test system for a high temperature and high pressure deep earth environment, comprising an MTS triaxial test machine and a control system connected with the MTS triaxial test machine;
   wherein the MTS triaxial test machine comprises a rigid frame, a high temperature and high pressure triaxial chamber, and a triaxial chamber base;
   the high temperature and high pressure triaxial chamber and the triaxial chamber base are arranged on the rigid frame, the high temperature and high pressure triaxial chamber is vertically opposite to the triaxial chamber base, a central axis of the high temperature and high pressure triaxial chamber coincides with a central axis of the triaxial chamber base;
   the control system comprises a workstation for data processing and a manual controller for controlling the workstation and a master controller;
   the workstation and the manual controller are synchronously connected with the master controller, the master controller is configured to control a confining pressure control system, a temperature control system, a seepage control system, and a loading control system;
   the MTS triaxial test machine further comprises an accurate triaxial force sensor limiting hole alignment device and an MTS triaxial force sensor dismounting and mounting supporting device; and
   the accurate triaxial force sensor limiting hole alignment device is arranged above the MTS triaxial force sensor dismounting and mounting supporting device.

2. The rock damage mechanics test system for the high temperature and high pressure deep earth environment of claim 1,
   wherein the MTS triaxial force sensor dismounting and mounting supporting device comprises a sensor lifting seat and a jack propped upon an MTS hydraulic servo table and configured to jack up the sensor lifting seat;
   the sensor lifting seat comprises a connecting disk connected with the jack, a support disk configured to support an MTS triaxial force sensor, and an operation channel for dismounting and mounting the MTS triaxial force sensor;
   a groove dented downwards is arranged on the connecting disk, the support disk is disposed in the groove and freely propped upon the connecting disk, and the support disk is radially limited by a side wall of the groove;
   both the connecting disk and the support disk are in an annular shape with a through hole arranged at a middle of the annular shape, and a control operation channel is formed by the through holes of the connecting disk and the support disk;
   a limiting device is arranged to prevent the MTS triaxial force sensor from disengaging from the support disk;
   the accurate triaxial force sensor limiting hole alignment device comprises a master rod for aligning with a central threaded hole and a secondary rod for aligning with a peripheral limiting hole;
   the master rod and the secondary rod are kept in a horizontal level, with a center-to-center distance between the master rod and the secondary rod equal to a center-to-center distance between the central threaded hole and the peripheral limiting hole;
   a stop sleeve is sleeved on the master rod to keep the master rod and the secondary rod in the horizontal level and make the center-to-center distance between the master rod and the secondary rod equal to the center-to-center distance between the central threaded hole and the peripheral limiting hole, and the stop sleeve is cylindrical;
   an upper corbel and a lower corbel are arranged on the stop sleeve, an end round hole axis of the upper corbel coincides with an end round hole axis of the lower corbel, and the end round hole axis of the upper corbel and the end round hole axis of the lower corbel are parallel to an axis of the master rod;
   a circular magnetic block is fixed on a secondary rod body, the circular magnetic block is configured to adsorb a hole alignment sleeve sleeved on the secondary rod body;
   an inner diameter of the hole alignment sleeve equals an inner diameter of a steel pin in an limiting hole arranged on the MTS triaxial force sensor;
   the hole alignment sleeve is marked with a first scale line and a second scale line, the first scale line corresponds to a relaxed or aligned state, and the second scale line corresponds to a contracted or aligning state; and
   the secondary rod comprises a secondary rod head body and the secondary rod body, and the secondary rod head body is connected with the secondary rod body by means of a spring.

3. The rock damage mechanics test system for the high temperature and high pressure deep earth environment of claim 2,
   wherein the secondary rod body and the upper corbel are fixed by means of a horizontal cylindrical pin, the master rod comprises a threaded rod, a first smooth cylinder, and a second smooth cylinder with a horizontal hole;
   the threaded rod can rotate into a threaded hole at a lower end of a solid rigid column of the MTS triaxial chamber, the first smooth cylinder is arranged in a middle of the master rod, and the stop sleeve is sleeved on the first smooth cylinder;
   a horizontal cylindrical short rod is arranged on the master rod by running through a round hole configured on the second smooth cylinder with a horizontal hole of the master rod;
   after an insertion of the horizontal cylindrical short rod into the round hole configured on the second smooth cylinder with the horizontal hole, the master rod is rotated to allow the second threaded rod to rotate into the threaded hole at the lower end of the solid rigid column of the MTS triaxial chamber; and
   the secondary rod body of the secondary rod is a cylindrical rod, a rolling steel ball is arranged in the secondary rod head body at an upper part of the secondary rod, and an outer diameter of the secondary rod head body is smaller than an inner diameter of the peripheral limiting hole.

4. The rock damage mechanics test system for the high temperature and high pressure deep earth environment of claim 3, wherein the spring is a cylindrical compression spring.

5. The rock damage mechanics test system for the high temperature and high pressure deep earth environment of claim 1,
   wherein a flange protruding upward is arranged at a middle of the groove in an axial direction, an inner wall of the groove and a bottom of the groove are enclosed to form an circular slideway;
   the flange is peripherally sleeved with a round rod slidable in the slideway, the support disk is freely propped upon the round rod, the limiting device is a stop collar, the stop collar is arranged above the connecting disk and detachably connected with the connecting disk, an inner wall of the stop collar and an upper surface of the support disk are enclosed to form an accommodating cavity fitting with the MTS triaxial force sensor, and a locking member is arranged on the stop collar to lock a relative position of the sensor;

the jack comprises a bottom pedestal, a top support table and a jacking mechanism arranged between the bottom pedestal and the top support table, and jacking mechanism is configured to drive the top support table to move up and down;

the jacking mechanism comprises four transmission rods, every two of the four transmission rods form an elbowed transmission member; each of the elbowed transmission members is provided with a connecting lug, two transmission rods of each of the elbowed transmission members are hinged with the connecting lug, the two elbowed transmission members are oppositely arranged to form a parallelogram structure with an equal side length, a first end of the parallelogram structure is hinged with a bottom lug arranged on the bottom pedestal, and a second end of the parallelogram structure is hinged with a top lug arranged on the top support table;

the connecting lug is provided for every two of the transmission rods, a first threaded rod is arranged diagonally for the parallelogram structure, the first threaded rod and the connecting lug are in a threaded connection to drive the elbowed transmission members to stretch and draw back; and a locating hole fitting with a central alignment pin of the MTS hydraulic servo table is arranged on the bottom pedestal.

6. The rock damage mechanics test system for the high temperature and high pressure deep earth environment of claim 5, wherein the inner wall of the stop collar extends inwards in a radial direction of the stop collar and protrudes into the groove of the connecting disk;

the support disk is vertically limited by a bottom surface of a protrusion of the stop collar extending inwards;

the locking member is a stop screw radially arranged along the stop collar and running through the stop collar, the stop screw and the stop collar are in a threaded connection;

the connecting lug is a grooved member with a first groove structure for accommodating a first transmission rod;

the bottom lug is a grooved member with a second groove structure for accommodating corresponding second transmission rod; and the top lug is also a grooved member with a third groove structure for accommodating a third transmission rod.

7. The rock damage mechanics test system for the high temperature and high pressure deep earth environment of claim 5, wherein the top support table is connected with the connecting disk by means of a group of support rods, the group of support rods are threaded, nuts fitting with threads of the group of support rods are fixedly attached to an upper surface and a lower surface of the top support table; and the group of support rods run through the top support table and are in a threaded connection with the nuts on the upper and lower surfaces of the top support table.

8. The rock damage mechanics test system for the high temperature and high pressure deep earth environment of claim 7, wherein a plane mirror is arranged on the upper surface of the top support table, and the operation channel and an orthographic projection of the plane mirror on the upper surface of the top support table are matched; and the plane mirror is hinged to the top support table by means of a spherical hinge.

* * * * *